United States Patent [19]

Mastrangelo et al.

[11] Patent Number: 6,093,700
[45] Date of Patent: *Jul. 25, 2000

[54] METHOD OF INDUCING AN IMMUNE RESPONSE USING VACCINIA VIRUS RECOMBINANTS ENCODING GM-CSF

[75] Inventors: Michael J. Mastrangelo, Jenkintown, Pa.; Edmund C. Lattime, Princeton, N.J.; David Berd, Wyncote; Laurence C. Eisenlohr, Merion, both of Pa.

[73] Assignee: Thomas Jefferson University, Philadelphia, Pa.

[*] Notice: This patent is subject to a terminal disclaimer.

[21] Appl. No.: 08/732,505

[22] PCT Filed: May 11, 1995

[86] PCT No.: PCT/US95/05908

§ 371 Date: Feb. 20, 1997

§ 102(e) Date: Feb. 20, 1997

[87] PCT Pub. No.: WO95/31105

PCT Pub. Date: Nov. 23, 1995

Related U.S. Application Data

[63] Continuation-in-part of application No. 08/242,268, filed as application No. PCT/US95/05968, Nov. 5, 1995.

[51] Int. Cl.[7] .......................... A61K 48/00; C12N 15/00
[52] U.S. Cl. ................................ 514/44; 435/320.1
[58] Field of Search .......................... 514/44; 435/320.1

[56] References Cited

FOREIGN PATENT DOCUMENTS

WO 92/19266  11/1992  European Pat. Off. .

OTHER PUBLICATIONS

Bash et al. (1993) Journal of Immunotherapy. vol. 14, 269–272.

Ramshaw et al. (1992) Immunological Reviews . vol. 127, 157–182.

Pincus et al. (1995) Biologicals. vol. 23, 159–164.

Hodge et al. (Nov. 1994) Cancer Research, vol. 54, 5552–5555.

Orkin et al. (1995) "Report and recommendations of the panel to assess the NIH investment in research on gene therapy".

Ross et al. (Sep. 1996) Human Gene Therapy, vol. 7, 1781–1790.

Bachmann et al. (1994) Current Opinion in Immunology, vol. 6, 320–326.

Masood et al. (1992) Blood, vol. 80, 115.

Vieweg et al. (1995) Cancer Investigation, vol. 13(2), 193–201.

James et al. (1991) Antiviral Chem. & Chemotherapy, vol. 2, 191–241.

Lathe et al., Nature (London) 326:878–880 (1987).

Bernards et al., Proc. Nat. Acad. Sci., USA 84:6854–6858 (1987).

Estin et al., Proc. nat. Acad. Sci., USA 85:1052–1056 (1988).

*Primary Examiner*—Scott D. Priebe
*Assistant Examiner*—Anne Marie S. Beckerleg
*Attorney, Agent, or Firm*—Seidel, Gonda, Lavorgna & Monaco, PC

[57] ABSTRACT

A method of inducing expression of immune active cytokines in tumors in situ is provided wherein a vaccinia virus vector capable of inducing expression of a selected cytokine is generated and injected into a tumor so that cells of the tumor express the selected cytokine. A method of enhancing immunity in a host by administration of a vaccinia virus vector is also provided. Methods of treating cancer by administration of these vaccinia virus vectors are also provided.

4 Claims, 1 Drawing Sheet

METHOD OF INDUCING AN IMMUNE RESPONSE USING VACCINIA VIRUS RECOMBINANTS ENCODING GM-CSF

This application is the U.S. National Phase of PCT/US95/05968, filed Nov. 5, 1995, which is a continuation-in-part of U.S. application Ser. No. 08/242,268, filed May 13, 1994, pending.

BACKGROUND OF THE INVENTION

Numerous attempts have been made to modulate a host's immune system as a means for treating cancers. Such attempts include: active immunotherapy using tumor or tumor antigen containing vaccines or immune active lymphokines; adoptive immunotherapy using a host's peripheral blood or tumor infiltrating lymphocytes expanded in culture and reinjected; passive immunotherapy by administration of monoclonal antibodies; and localized immunotherapy using intralesional administration of agents such as Bacillus Calmette-Guerin (BCG). The most effective of these approaches has been localized therapy with BCG for melanoma metastasis to the skin and superficial bladder cancer. While the mechanism of action of BCG is not completely understood, studies clearly show that successful immunotherapy of this type is associated with recruitment of T cells to the tumor.

Cytokines such as the interleukins are important mediators in cell-mediated immune responses in a host. The cell-mediated immune response ("local immune responses") is produced by thymus derived lymphocytes or T-cells. T-cells detect the presence of invading pathogens through a recognition system referred to as the T-cell antigen receptor. Upon detection of an antigen, T-cells direct the release of multiple T-cell lymphokines including, but not limited to, the interleukin-2 family (IL-2). IL-2 is a T-cell growth factor which promotes the production of many more T-cells sensitive to the particular antigen. This production constitutes a clone of T-cells. The sensitized T-cells attach to cells containing the antigen. T-cells carry out a variety of regulatory and defense functions and play a central role in immunologic responses. When stimulated to produce a cell-mediated immune response, some T-cells respond by acting as killer cells, killing the host's own cells when these have become infected with virus and possibly when they become cancerous and therefore foreign. Some T-cells respond by stimulating B cells while other T-cells respond by suppressing immune responses.

Examples of other interleukins which are mediators in cell-mediated immune responses include interferon-γ (IFN-γ), granulocyte-macrophage colony stimulating factor (GM-CSF), interleukin-4 (IL-4), interleukin-5 (IL-5) and interleukin-12 (IL-12). IFN-γ activates macrophages and enhances expression of immune-reactive antigens on tumor cells. GM-CSF activates macrophages and stimulates macrophage and dendrite cell recruitment and differentiation. IL-4 is a T cell derived helper lymphokine which participates in the regulation of growth and differentiation of B and T cells. IL-5 is a T cell derived lymphokine which has its primary effects on the expansion of eosinophils. There is evidence which suggests that eosinophils, when recruited to a tumor site, may have direct anti-tumor effects. IL-12 is a heterodimeric lymphokine initially purified from the conditioned medium of a human B lymphoblastoid cell line. Murine IL-12 has now been cloned and expressed. IL-12 stimulation has been shown to enhance antigen presentation and the cytolytic activity of natural killer cells.

The value of cytokine-based gene therapy was suggested in preclinical murine studies. Inoculation of mice with experimental tumors transfected with genes for tumor necrosis factor (Asher AL, et al., *J. Immunol.* 1991 146:3227), interleukin-2 (Fearon ER, et al., *Cell* 1990 60:397), and IL-4 (Golumbek PT, et al., *Science* 1991 254:713) resulted in growth and subsequent rejection of the injected tumor. In many cases the mice were shown to generate a systemic anti-tumor response. IL-4 transfected tumors regressed and lead to the regression of admixed non-transfected tumors in mice (Tepper PI, et al., *Cell* 1989 57:503). This immunotherapy was also effective in nu/nu mice demonstrating a non-T cell component which may contribute to localized therapy. IL-4 transfected RENCA cells have been shown to generate specific T cell immunity to the tumor, and result in elimination of pre-existing non-local tumor growth (Golumbek PT, et al., *Science* 1991 254:713).

Current approaches to this form of therapy involve the growth and stabile gene modification of tumor cells to produce cytokines, their expansion in vitro, and reinjection into the host. While this type of therapy may be feasible in experimental systems, the lack of ability to grow the majority of tumors in vitro, the requirements for in vitro genetic modification of each patient's tumor, and the reinjection of viable tumor into the patient limit the clinical applicability of the approach.

It has now been found that expression of immune active cytokines in tumors can be induced in situ by administration of a vaccinia virus vector. These vaccinia virus vectors can be administered to animals suffering from cancer as a treatment. The vaccinia virus vectors of the present invention are also useful in enhancing immunity to parasites and other invading pathogens which alone fail to invoke an effective host immune response.

SUMMARY OF THE INVENTION

An object of the present invention is to provide a method of inducing expression of immune active cytokines in tumors in situ which comprises generating a vaccinia virus vector capable of inducing expression of a selected cytokine and injecting the vaccinia virus vector into a tumor so that cells of the tumor express the selected cytokine.

Another object of the present invention is to provide a method of enhancing immunity in a host which comprises generating a vaccinia virus vector capable of inducing expression of a selected cytokine and injecting the vaccinia virus vector into a host so that cells of the host express the selected cytokine.

A final object of the present invention is to provide a method of treating cancer which comprises administering to an animal suffering from cancer an amount of a vaccinia virus vector capable of inducing an immune response to the cancer in the animal.

DETAILED DESCRIPTION OF THE INVENTION

Figure 1:
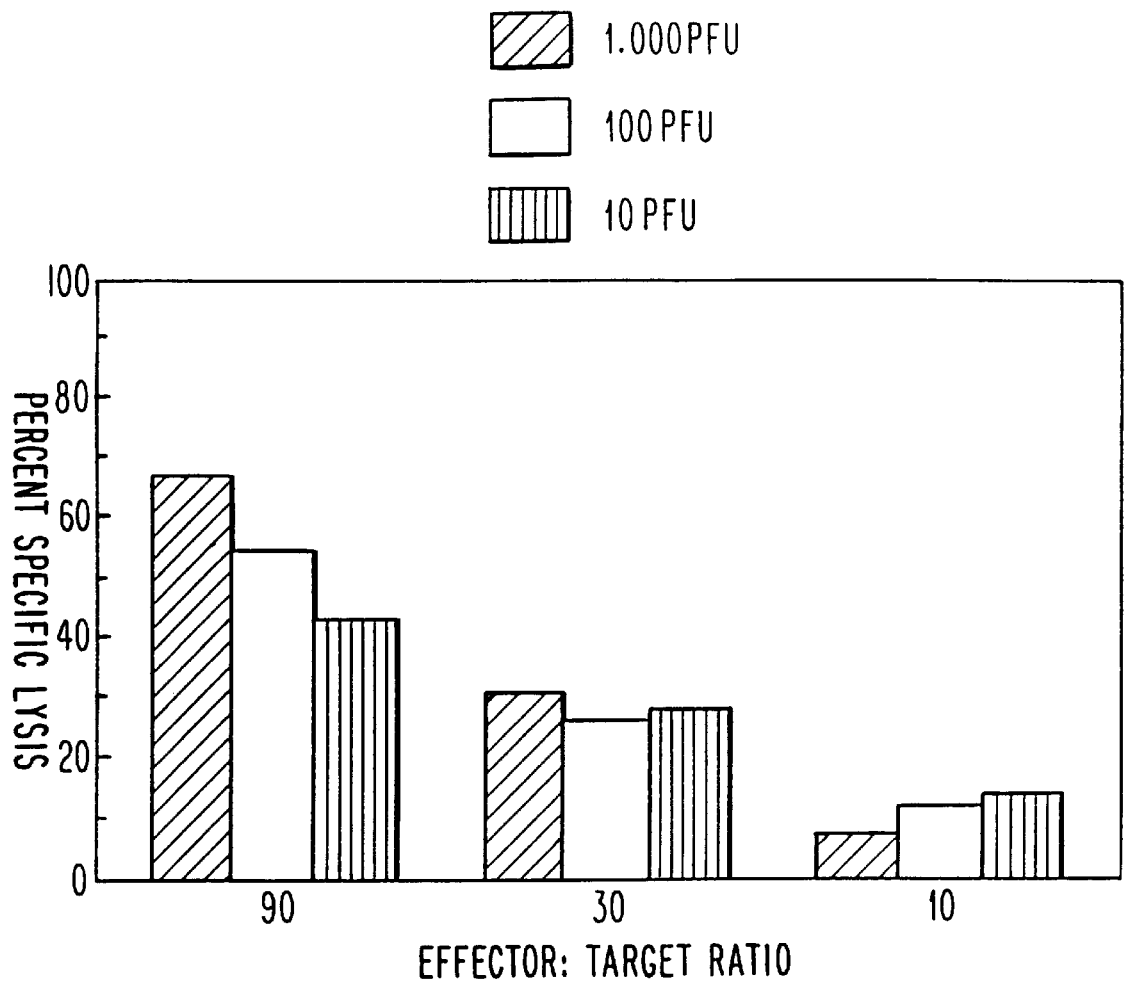
FIG. 1 is a bar graph showing systemic immunity resulting from intravesical instillation of the vaccinia virus vector (VAC). Mice received intravesical instillation of VAC at 10, 100 and 1,000 plaque forming units (pfu). Two weeks later, mice spleens were removed and tested for their ability to lyse VAC-infected MB-49 cells.

It has been clearly demonstrated in a number of studies that generation of effective T-cell specific immunity can result in the elimination of tumors. In vitro transduced cytokine and viral genes expressed by tumors have resulted in the elimination of transfected tumors and enhanced T cell mediated immunity to non-transduced tumors. Expression of immune accessory molecules such as B7.1 and B7.2 has also been demonstrated to enhance anti-tumor immunity. However, in vitro manipulations of tumors to express selected molecules has its limitations, particularly in the clinical setting. Genetic modification of tumors for cellular vaccines is dependent upon and limited by the ability to resect and to grow each patient's tumor in vitro and reinjection of viable, modified tumor.

A method has now been developed for in vivo gene delivery of a gene which expresses an immune active cytokine which obviates the need for in vitro manipulations of tumor cells thus enhancing the clinical applicability of this therapeutic approach. In the present invention, a method of inducing expression of immune active cytokines in tumors in situ is provided which comprises generating a vaccinia virus vector capable of inducing expression of a selected cytokine and injecting the vaccinia virus vector into a tumor so that cells of the tumor produce the selected cytokine. By the term "inducing" or "induces" it is meant that the level of expression of the cytokine is measurable by methods well known in the art and that the level of expression of the cytokine results in an immune response. By the term "immune active cytokine" or "selected cytokine" it is meant to refer to any cytokine associated with an immune response leading to tumor destruction. Examples of such cytokines include, but are not limited to, interferon-γ (IFN-γ), granulocyte-macrophage colony stimulating factor (GM-CSF), interleukin-2 (IL-2), interleukin-4(IL-4), interleukin-5 (IL-5), and interleukin-12 (IL-12). The vaccinia virus vector may further comprise a gene for an immune accessory molecule such as B7.1 or B7.2. By "immune accessory molecule" it is meant a molecule which in conjunction with the immune active cytokine can make the tumor more immunogenic. Unlike in vitro methods of gene transfer, infection and transfection using recombinant vaccinia has been found to be a simple, rapid and highly efficient procedure. Vaccinia recombinants can efficiently deliver antigens to the class I presentation pathway and have been proposed as feasible vectors for expressing protective antigens for vaccine delivery. Moss B and Flexner C., "Vaccinia virus expression vector", *Ann. Rev. Immunol.* 1987 5:305–324. The potential utility of vaccinia recombinants for intravesical gene therapy aimed at enhancing the immunogenicity of bladder tumor cells was suggested by Lee SS, et al. *Proc. Am. Assoc. Cancer* March 1993 34:337. It has now been found that these viral vectors can be used in a method of stimulating the immune system by inducing expression of cytokines at a tumor site.

Vaccinia virus, a double stranded DNA poxvirus, has been well characterized since its successful use as a live vaccine to prevent smallpox. As a versatile eukaryotic expression vector, vaccinia virus can be genetically constructed to contain large fragments of foreign DNA (up to 25 kd) which have no effect on viral replication. Immunization with recombinant vaccinia can induce protective responses to the foreign gene(s) expressed. In the present invention a vaccinia virus vector (VAC) capable of inducing expression of a selected gene is generated in accordance with methods well known in the art. The vaccinia virus vector may further comprise genes encoding immune accessory molecules which in conjunction with the immune active cytokine can make the tumor more immunogenic.

In a preferred embodiment, a foreign gene of interest, preferably a gene for a selected cytokine, more preferably the gene for IFN-γ, GM-CSF, IL-4, IL-5 or IL-12, is first placed behind a promoter, preferably a VAC promoter, in a plasmid that can be inserted into the VAC genome by homologous recombination. Other genes which may be incorporated into the vector include, but are not limited to, genes encoding immune accessory molecules such as B7.1 and B7.2, or genes which inhibit IL-10 production. It has recently been found that both human melanoma and bladder cancer produce the immunosuppressive cytokine IL-10. Thus, inhibition of this cytokine is believed to enhance the immunogenicity of tumors. Inhibition of the expression of IL-10 has been demonstrated through the use of antisense oligonucleotides complementary to the IL-10 DNA or mRNA in other cells. The ability to express an antisense oligonucleotide complementary to the IL-10 DNA or mRNA can be incorporated into vaccinia virus vectors of the present invention to inhibit IL-10 production in tumor cells, thus enhancing the immunogenicity of these tumors.

Successful insertion of the selected gene in the plasmid is confirmed by exploiting the high transfectability of certain cell lines following vaccinia infection. After 30 minutes of exposure to wild-type vaccinia at a multiplicity of 10:1, mouse L929 cells are transfected with a plasmid DNA-lipofectin (Gibco/BRL, Bethesda, Md.) mixture. Within hours of transfection, abundant amounts of gene product can be observed, with a majority of the cells expressing the protein. The generation of the desired gene can be detected using standard immunodetection techniques such as immunoprecipitation of metabolically-labeled proteins or western clot of cell-extracts. Further, supernatants from the infected/transfected cells are tested for biological activities associated with the various cytokines or other proteins. After confirmation that the gene of interest has been correctly inserted and encodes a biologically active protein, the plasmid is recombined in the VAC genome. The plasmids are designed such that the gene of interest is inserted between the up- and downstream halves of the VAC thymidine kinase gene. Following infection of CV-1 monkey kidney cells with non-recombinant virus, the plasmid is delivered using calcium phosphate precipitation. In a portion of the cells, the plasmid recombines into the vaccinia genome, disrupting the thymidine kinase gene. The resulting recombinants are then selected from wild-type by growth in thymidine kinase negative 143B human osteosarcoma cells in the presence of bromodeoxyuridine. It is preferred that the Wyeth strain of vaccinia, available from the Centers for Disease Control in Atlanta, Ga. (CDC) be used as this strain was used for small pox vaccinations in the United States. However, attenuated strains of vaccinia may also be used if immunogenicity following attenuation is not significantly compromised.

Susceptibility of cells to the vaccinia virus was demonstrated in in vitro experiments in both murine and human tumor cells. Both type of cells were infected/transfected by vaccinia recombinants. Significant infection/transfection of established tumors in mice was also observed following intravesical administration. Systemic immunity to vaccinia did not inhibit tumor transfection by intravesically instilled vaccinia recombinants.

The safety and maintained function of the viral gene over repeated administrations have also been demonstrated in humans. Five patients with dermal, subcutaneous and/or lymph node metastases from cutaneous melanoma were vaccinated with wild-type vaccinia virus and, four days later, began intratumoral injections of the same vaccine. Escalating doses of up to $10^7$ pfu were safely administered repeatedly with only local and mild systemic reactions. Four of the patients developed anti-vaccinia virus antibody titers ≧1/3200. With rising antibody titers, local and systemic reactions decreased. One patient with a large exophytic lesion experienced dramatic tumor regression with multiple injections of $10^7$ pfu of virus. Sequential biopsies of this lesion over a two month period demonstrated repeated infection over successful production of viral gene protein (E3L) despite anti-viral antibody titers as high as 1/12,800. This time interval is adequate to allow generation of anti-tumor immunity. It is believed that a vector comprising a cytokine gene would function similarly and mediate an immunoadjuvant effect.

The vaccinia virus vectors of the present invention can also be used to enhance immunity in a host. In the present invention methods of enhancing immunity in a host are provided which comprise generating a vaccinia virus vector capable of inducing expression of a selected cytokine and injecting the vaccinia virus vector into a host so that cells of the host express the selected cytokine. By "host" it is meant to include, but is not limited to, mammals, fish, amphibians, reptiles, birds, marsupials, and most preferably, humans. This method is also useful in enhancing a host's immune response to parasites and other invading pathogens which alone may not invoke an immune response.

In addition, the vaccinia virus vectors of the present invention can be used to mediate cytokine gene transfer into tumors with resultant production of soluble product. For example, a recombinant vaccinia virus containing the murine GM-CSF gene under the control of the early/late P7.5 vaccinia promoter (VV-GM) was constructed. VV-GM infected murine melanoma (B16.F10) and bladder (MB49) tumors were shown to produce high levels of biologically active cytokine as determined by propagation of bone marrow CFU-GM and by ELISA assay. Significant levels of GM-CSF were found in the supernatant as soon as 6 hours following infection. This increased cytokine secretion of the tumor cells can lead to tumor specific immunity and therapeutic anti-tumor effects.

Accordingly, the vectors and methods of the present invention are useful in the treatment of cancer. Methods of treating cancer are provided comprising administering to an animal suffering from cancer an amount of a vaccinia virus vector capable of inducing an immune response to the cancer in the animal. In a preferred embodiment, the vaccinia virus vector used comprises at least one gene for expression of a cytokine, preferably the gene for IFN-γ, GM-CSF, IL-4, IL-5 or IL-12. In this treatment, the vaccinia virus vector is placed in contact with the tumor in situ either by intravesical administration or by direct injection into the tumor. Therefore, this method is especially useful in treating cancers such as bladder cancer, head cancer, neck cancer, melanoma, and other cancers which grow as accessible masses and are amenable to these routes of administration.

The susceptibility of human prostatic carcinoma cells to vaccinia was also examined utilizing a recombinant vector encoding the human influenza hemagglutinin antigen HA. In vitro exposure of the prostatic cell lines LNCAP and PC3 to the virus followed by immunohistochemical staining of the encoded HA protein demonstrated a high efficiency in tumor infection/transfection. Thus, the vaccinia virus vectors of the present invention can also be used in the localized therapy of prostate cancer.

The vaccinia virus vectors of the present invention are administered in a vaccine formulation comprising an effective concentration of vaccinia virus vector and a pharmaceutically acceptable carrier. By "effective concentration" it is meant an amount of vaccinia virus vector which when administered to a tumor results in measurable expression of the selected cytokine and an enhanced immune response. Such amounts can be routinely determined by one of skill in the art in accordance with this disclosure. Pharmaceutically acceptable carriers include, but are not limited to saline solutions and buffered solutions. Suitable pharmaceutically acceptable carriers are well known in the art and are described for example in Gennaro, Alfonso, Ed., *Remington's Pharmaceutical Sciences,* 18th Edition 1990, Mack Publishing Co., Easton, Pa., a standard reference text in this field. Pharmaceutical carriers may be selected in accordance with the intended route of administration and the standard pharmaceutical practice. The vaccine formulation may further comprise an adjuvant. Adjuvants are substances which are added to therapeutic or prophylactic agents, for example vaccines or antigens used for immunization, to stimulate the immune response. Use of adjuvants in vaccines to enhance an immune response is well known in the art.

The present invention is further illustrated by the following nonlimiting examples.

EXAMPLES

Example 1

Recombinant Vaccinia Virus

Recombinant vaccinia viruses H1-VAC and NP-VAC expressing the hemagglutinin (H1) and nucleoprotein (NP) genes derived from influenza virus A/PR8/34 were used. Expression of both influenza polypeptides is under the control of the early/late 7.5 K promoter. Viral stocks quantitated in pfu were maintained in BSS/BSA at −70° C. until use.

Example 2

Cell Lines

The transitional cell carcinoma (TCC) cell lines MB-49 of C57BL/6 origin, MBT-2 of C3H origin and the human T24 bladder carcinoma and H1 human melanoma were used.

Example 3

Antibodies, Reagents and Staining

Supernatants from hybridoma cell lines specific for the influenza A hemagglutinin (H28-E23) and nucleoprotein antigens (HB65) were used to stain cells and tissues. The virus infected bladder tumor cells and bladder urothelium sections were fixed with cold acetone and blocked with 0.1% fetal calf serum. HA and NP were detected with primary mouse antibody and biotin labeled antimouse IgG as the second antibody plus avidin-horseradish peroxidase (HRP) and 3.3 DAB substrate (Sigma, St. Louis, Mo.) or avidin-biotin-complex method (ABC-AP) plus alkaline phosphatase with Fast red substrate (Vector Laboratories, Inc., Burlingame, Calif.). Tissue sections were counterstained with hematoxylin. In addition, hematoxylin-eosin (H&E) stained sections were prepared.

Example 4

In vitro Assessment of Viral Infection and Transfection

Cells ($2 \times 10^6$) from each cell line described in Example 2 were plated into a 24 well flat bottom plate (Fisher, Pittsburgh, Pa.). Plates were incubated overnight, washed with phosphate buffered saline (PBS) and infected with H1-VAC or NP-VAC (10 pfu/cell) in BSS/BSA by incubating at 37° C., 9% $CO_2$ for 1 hour with rocking every 15 minutes. Virus was aspirated, media was added and the plate were incubated for another 4 hours. The cells were fixed with 1:1 acetone:methanol for 1 minute and washed with PBS before immunohistochemical staining. Uninfected and recombinant virus infected L929 fibroblasts, which are known to be susceptible to vaccinia virus infection, were used as a negative and positive control, respectively.

The murine MBT-2 and MB-49 TCC cells were infected in vitro with H1-VAC. When compared to uninfected tumor cells, immunohistochemical staining with specific antibodies showed positive expression for encoded HA or NP antigens indicated by the cytoplasmic staining of virus infected TCC cells. In addition, the human bladder tumor cell line T24 and a human melanoma line were similarly infected in vitro.

Example 5

In vivo Assessment of Virus Infection and Transfection

Female mice, 4–6 weeks of age, were purchased from the Jackson Laboratory, Bar Harbor, Me. The mice were intravesically instilled with recombinant vaccinia virus. Mice were anesthetized, catheterized via the urethra, then cauterized with a cautery wire (Birtcher Hyfricator, El Monte, Calif.) by applying a single 1 second pulse at 1 watt. After removal of the cautery wire, the bladders were instilled with $10^4$ MB49 cells to establish intravesical growth of a tumor or either 10, 100 or 1,000 pfu of vaccinia virus recombinants in PBS. At 8 and 22 hours following instillation, mice were sacrificed and bladders were removed and frozen in OCT media (Fisher) in liquid nitrogen. Bladder samples were stored at −70° C. until sectioned.

Mice, pre-immunized intraperitoneally with wild-type WR vaccinia ($10^7$ pfu), were implanted intravesically with MB-49 tumor cells. Two weeks following tumor development, a single intravesical instillation of NP-VAC ($2\times10^6$ pfu, shown not to have systemic toxicity in preimmune mice) was given. At 8 and 22 hours post-instillation, bladders were removed, sectioned and stained. In vivo expression of encoded NP was demonstrated at 22 hours after instillation. Similar results were seen at the 8 hour time point.

Example 6

Cytotoxic T Lymphocyte Analysis

Cytotoxic T Lymphocyte (CTL) responses to intravesical infection by vaccinia recombinants were determined by a 4 hour $^{51}$Cr assay. Spleens of virus infected mice were isolated at 2 weeks post-intravesical instillation, restimulated in vitro with live virus infected syngeneic spleen stimulators (3:1) and cultured for 7 days at 37° C., 5% $CO_2$. The responder cells were assayed for cytotoxicity on $^{51}$Cr labeled vaccinia virus infected MB49 tumor targets at effector to target ratios indicated. Percent specific lysis was calculated as follows: (cpm experimental release-cpm spontaneous release)/(total release-spontaneous release)×100. Spleens of intravesically infected C57BL/6 mice were tested for antigen specific killing of vaccinia virus infected MB-49 bladder tumor target cells in 4 hour chromium release assays. No virus-induced target lysis was seen in the 4 hour assay and virus-specific CTL did not lyse uninfected targets. As shown in FIG. 1, concentrations as low as 10 pfu intravesically were sufficient to induce a systemic anti-vaccinia CTL response. When the dose of intravesical vaccinia was titrated, concentrations of greater than $10^5$ pfu per mouse were lethal to nonimmunized mice, which died within 5–6 days post-instillation. In contrast, mice receiving a single intravesical concentration less than $10^5$ pfu appeared normal and survived greater than 2 weeks post-instillation. Mice made preimmune with an intraperitoneal injection of wild-type WR vaccinia virus ($10^7$ pfu) demonstrated no morbidity at intravesical concentrations as high as $2\times10^6$ pfu of vaccinia recombinants per mouse.

C57BL/6 female mice were given a single intravesical instillation with vaccinia recombinant H1-VAC or NP-VAC ($10^4$ pfu) to confirm infection of the urothelium. The mice were sacrificed, post instillation, and their bladders were recovered for sectioning and staining. Analysis of the bladder wall by routine pathology procedures using H & E stained slides demonstrated that urothelial cells lining the bladder lumen were virus infected as indicated by characteristic morphologic changes including cell enlargement, nuclear and cytoplasmic vacuolization, as well as atypical chromatin pattern.

Example 7

Human Study Using Intratumoral Vaccinia Injections as a Vector for Gene Transfer Patients in this study each had histologically documented, surgically incurable melanoma with at least one dermal, subcutaneous or lymph node metastasis which was evaluable for local response and accessible for injection. Eligible patients were fully ambulatory with or without minor tumor related symptoms, had a life expectancy of six or more months and were at least four weeks since surgery (requiring general anesthesia) and eight weeks since chemotherapy or radiation therapy. All patients were immunocompetent as demonstrated by one or more positive cutaneous delayed-type hypersensitivity reactions to recall microbial antigens or to dinitrofluorobenzene after sensitization.

Patients were administered Dryvax (Wyeth-Ayerst Laboratories, Philadelphia, Pa.) supplied by the Center for Disease Control (Atlanta, Ga.) in a lyophilized state. When reconstituted as directed, the resultant product contains 25 million pfu in a volume of 0.25 ml.

Each patient was vaccinated, using a standard multipuncture method with a bifurcated vaccination needle, on the skin of the deltoid area which in all cases was a tumor free extremity with intact regional lymph nodes. The vaccination site was evaluated visually on day 4 to confirm that a major local reaction (erythematous papule with vesiculation and pustule formation) was in progress. Tumor treatment commenced on day 4. Dermal, subcutaneous and/or lymph node metastases were infiltrated with wild-type vaccinia virus by intralesional injection using a 25 gauge needle (volume of injection ranged from 0.05 to 0.1 ml). Treatment was repeated approximately twice weekly.

Regression of injected and uninjected lesions was judged by visual inspection and/or ultrasonography. Ultrasonography was performed using a 10.0 MHz linear probe (Advanced Technology Laboratories, Inc., Bothel, Wash.) with direct contact scanning of the surface of the mass as well as scanning with a stand-off pad (Parker Laboratories, Inc., Orange, N.J.). All masses were imaged in the sagittal and axial planes. Tumor location, depth of penetration and sonographic textural appearance were determined. Tumors were measured in millimeters (mm), with the sagittal (S) and anteroposterior (AP) dimensions taken from the sagittal image with the greatest dimension. The tumor width (W) was obtained from the transverse plane. Lesional response were categorized as complete (no clinically evident residual tumor), partial (≧50% reduction in tumor volume) or none (all others).

Punch biopsies were also performed using conventional sterile dermatologic techniques. One half of the material was fixed in formalin, paraffin embedded and sections stained with hematoxylin and eosin for routine histology. The remaining tissue was halved again for transmission electron microscopy (EM) and immunohistochemical analysis. Tissue was either fixed in 2% glutaraldehyde or embedded in OCT (Fisher Scientific, Pittsburgh, Pa.) and snap frozen using liquid nitrogen. Frozen tissue was subsequently sectioned at 5 microns thickness with a cryostat, fixed in cold acetone, blocked with PBS with 5% fetal calf serum (FCS) and stained with the antibody TW2.3 which is specific for an early gene product of vaccinia virus replication (E3L). As E3L is a non-structural viral protein, positive antibody staining is indicative of active infection.

To measure serum titers for anti-vaccinia virus antibody, ninety-six well plates were coated with a 10 $\mu$g/ml protein extract obtained from cultures of human melanoma cell lines infected for 6 hours with the Wyeth strain of vaccinia virus. Following blocking with PBS plus FCS, dilution series of patient sera pre- and post-immunization were added to the wells, incubated for two hours and the plates washed. Serum anti-vaccinia virus antibodies were visualized using a peroxidase labeled anti-human IgG heavy and light chain second reagent and orthophenyldiamine substrate. Titers were read as the reciprocal serum dilution yielding 50% maximum absorbance in the assay.

Example 8

Intralesional Infection of Human Melanoma Cells by Vaccinia Virus

One patient, a sixty-five year old white female, was first diagnosed with a primary melanoma (1 mm, level 4) of the right calf with satellite lesions in 1983. The primary lesion was excised and the dermal satellites successfully treated with intratumoral BCG. The patient did well until 1992 when two dermal/sc lesions appeared on the calf and failed to respond to intratumoral BCG, systemic R24 or chemotherapy. Vaccinia treatment was initiated with a standard immunization (250,000 pfu topically, 15 punctures). On day 4 of treatment, when it was determined that a take was clearly in progress, intralesional vaccinia was commenced. A single metastatic lesion was injected 19 times over 88 elapsed days with a total of $14\times10^7$ pfu (Wyeth). Several biopsies showed progressively intense infiltration of the tumor with lymphocytes and tumor regression. EM and immunohistological staining for vaccinia gene products showed successful viral infection of tumor cells in the presence of substantial anti-vaccinia antibody titers.

Example 9

Clinical Trials

Patients are administered small pox vaccine (Dryvax, Wyeth Laboratories, by scarification. Immunity to the vaccine is demonstrated by a major reaction characterized by pustule formation at the vaccination site and the detection of circulating anti-vaccinia antibody. Patients exhibiting both response are eligible for localized treatment with the cytokine producing vaccinia vector.

Patients are treated with increasing doses of the vaccinia over a several week period by local (intratumoral or topical such as intravesical) administration. In the case of melanoma, head and neck, and other tumors which grow as accessible solid masses at the primary and or metastatic sites, the vaccinia is injected into the tumor using a syringe and needle. In the case of bladder cancer, the vaccinia is instilled onto the bladder (intravesically) using a catheter.

Patients are observed at frequent intervals for signs of toxicity, and tumor response is gauged by measuring the injected and non-injected tumor masses for signs of shrinkage by direct visualization or radiologic (ultrasound, X-ray, MRI, etc.) methods.

Evidence of systemic antitumor immunity will be determined using in vitro techniques which measure the direct interaction of lymphocytes and tumor cells. Measurements of antitumor immunity are readily accomplished by persons with skill in this field.

What is claimed is:

1. A method of expressing granulocyte-macrophage colony stimulating factor in tumors in situ comprising: a) generating a vaccinia virus vector encoding a gene for granulocyte-macrophage colony stimulating factor operably linked to transcriptional regulatory elements; and b) injecting said vaccinia virus into a tumor so that cells of the tumor express granulocyte-macrophage colony stimulating factor.

2. A method of producing regression of a tumor in a mammal having cancer comprising administering to the tumor in said mammal a vaccinia virus vector encoding a gene for granulocyte-macrophage colony stimulating factor operably linked to transcriptional regulatory elements in an amount capable of inducing an immune response to the tumor in the mammal such that the tumor regresses.

3. The method of claim 2 wherein the animal has cancer comprising bladder cancer, head cancer, neck cancer or melanoma.

4. The method of claim 2 wherein the animal has prostate cancer.

* * * * *